United States Patent [19] [11] Patent Number: 4,796,607
Allred, III et al. [45] Date of Patent: Jan. 10, 1989

[54] ENDOSCOPE STEERING SECTION

[75] Inventors: Jimmie B. Allred, III, Skaneateles; Richard Bingham, Auburn, both of N.Y.

[73] Assignee: Welch Allyn, Inc., Skaneateles Falls, N.Y.

[21] Appl. No.: 78,714

[22] Filed: Jul. 28, 1987

[51] Int. Cl.$^4$ .............................................. A61B 1/00
[52] U.S. Cl. ......................................... 128/4; 138/120
[58] Field of Search ....................... 128/4, 6; 138/120

[56] References Cited

U.S. PATENT DOCUMENTS

| | | | |
|---|---|---|---|
| 3,190,286 | 6/1965 | Stokes | 128/6 |
| 3,557,780 | 1/1971 | Sato | 128/4 |
| 3,583,393 | 6/1971 | Takahashi | 128/4 |
| 3,610,231 | 10/1971 | Takahashi | 128/6 |
| 3,669,098 | 6/1972 | Takahashi | 128/6 |
| 3,739,770 | 6/1973 | Mori | 128/6 |
| 3,799,151 | 3/1974 | Fukaumi et al. | 128/6 |
| 4,347,837 | 9/1982 | Hosono | 128/6 |
| 4,700,693 | 10/1987 | Lia et al. | 128/4 |

*Primary Examiner*—William H. Grieb
*Attorney, Agent, or Firm*—Wall and Roehrig

[57] ABSTRACT

A steering section for an endoscope or borescope employs a plurality of steering cables that pass through peripheral bores of axially aligned flat washers. Spacer beads are strung on the cables between the washers to define hinge points for the bending of the steering section. The spacer beads are tapered beads having a relatively wide base and relatively small, flat nose surface. A through-passage in the bead has a relatively narrow nose portion with a small clearance with respect to the steering cable, and a tapered or countersunk portion that expands basewards and prevents the spacer bead from binding the cable.

13 Claims, 2 Drawing Sheets

ENDOSCOPE STEERING SECTION

BACKGROUND OF THE INVENTION

This invention relates to controllably bendable tube assemblies, and especially to a hollow steering section of a borescope or endoscope.

An endoscope is generally characterized as an elongated flexible tube with a viewing head in its distal or forward end, and a control section at its proximal end for controlling or steering the distal end. In such an endoscope, a bendable tube steering section is provided at the distal end adjacent to the viewing head. One or two pairs of control cables extend through the bendable tube steering section and the remainder of the flexible tube, and these cables connect with a steering control in the control section. One or both pairs of these cables are displaced in order to bend the bendable tube steering section to facilitate the inspection of an object.

An endoscope is typically inserted into the body cavity of a patient to investigate visually the tissues within the cavity. For example, an endoscope can be inserted into the colon or stomach, or into the lung of a patient. Because the esophagus, bronchii and the colon are narrow, tortuous passageways, the steering section must be bent rather precisely, and the bend should occur as close to the head as possible, in order to obtain the necessary penetration without damaging the patient's tissues. It is most desireable that the slack in the cable be kept to an absolute minimum, so that steering can be controlled precisely.

A borescope is a similar device, but intended for visual inspection of a mechanical device, such as a jet engine or turbine, where it would be difficult or impossible to examine the device's internal elements. The borescope needs to be insertable into narrow tortuous passageways, and must observe similar steering and bending considerations.

A number of types of steering mechanisms are known. For example, helically coiled strips are employed in endoscopes or borescopes as described in U.S. Pat. Nos. 3,610,231 and 3,739,770. Steering sections having thin-walled cylindrical segments or bands that are joined by means of pins or bifurcations or other similar articulations such that the segments are rockable on one another, are described in U.S. Pat. Nos. 3,583,393; 3,669,098; 3,799,151; and 4,347,837. A previously-proposed endoscope that had a provision to control the degree of bending is described in U.S. Pat. No. 3,557,780.

The steering mechanisms for these previously-proposed endoscopes are rather elaborate structures, with many parts that can fail and which are relatively expensive to produce. Further, in many cases it has been necessary to provide the cables with a significant amount of slack because the steering sections bend at discrete points, and not in a perfectly smooth curve.

U.S. Patent Application Ser. No. 806,667, filed Dec. 9, 1985, now U.S. Pat. No. 4,700,693, granted Oct. 20, 1987, and having a common assignee herewith, addresses the above problem. The disclosure in that patent application is incorporated herein by reference.

In the steering section of the endoscope or borescope described in Application Ser. No. 806,667, the steering section has, within its flexible sheath, a plurality of axially aligned washers, each having a central passage and a number of peripheral bores. Pairs of these peripheral bores are disposed generally diametrically opposite each other. The steering cables pass through the respective axially aligned peripheral bores of the washers, and spacing structure is disposed at the location of predetermined ones of these peripheral bores to define bending locations for the steering section, such that the displacement of certain pairs of the steering cables results in bending of the steering section in one plane or another. As disclosed in that patent application, the washers are flat washers, and the spacer structure includes pairs of hemispherical beads that are disposed in nose-to-nose fashion over the respective cables between successive washers. The beads have their spherical surfaces facing one another, and their flat surfaces facing outward against their associated washers.

The upshot of this construction is that when the steering section is bent, the spherical surfaces of the hemispherical beads should roll over one another to achieve smooth bending without a significant amount of slack in the cable.

Unfortunately, with this design, the hemispherical spacer beads tended to degrade in service over time. The basic reason for this is that the steering cable had to have a significantly smaller diameter than the diameter of the through-bore of the beads to achieve proper clearance for the cable. Because of the difference in diameters of the cable and the spacer bead through-bores, there is a tendency for the hemispherical spacer beads to shift off axis by the amount of the clearance. When the spacer beads rock over one another, the intersecting edges of the through-holes cut into one another in the radially displaced beads. This eventually works into a saddle and binds on the cable.

In order to avoid this problem, it was necessary to provide a relatively wide bearing surface at the facing noses of the beads to compensate for this lateral sliding of the spacers relative to one another. However, if the nose surface is wide enough to compensate for the entire clearance between the steering cable and the spacer bead through-bores, then as one spacer bead tilts with respect to another as the steering section is bent, the required length of the cable is increased. Since the actual cable length does not increase, the effect of this is to tighten the cable when the steering section is deflected, and thereby increase steering forces.

Of course, a smaller bearing nose surface could be employed if there were a smaller diametrical clearance between the cable and spacer bead, but in that case the cable would bind against the spacer beads when the spacers tilted with respect to each other.

OBJECTS AND SUMMARY OF THE INVENTION

Accordingly, it is an object of this invention to provide an endoscope bendable steering section which avoids the drawbacks of the prior art.

It is a further object of this invention to provide a steering section which keeps the slack or play in the steering cables to a minimum, but which will not bind the steering cables when bent.

It is a still further object of this invention to provide a bendable steering section with smooth, crisp, and precise bending action.

As aforesaid, this invention resides in the steerable endoscope or borescope of the type having a viewing head and a cable-bendable steering section disposed proximally of the viewing head. The steering section has a flexible sheath, a plurality of washers, with each of the washers having a central passage and a plurality of peripheral bores therethrough, a plurality of steering cables passing through respective axially aligned ones of the peripheral bores of the washers, and pairs of spacer beads disposed in nose-to-nose fashion over the steering cables at the locations between certain ones of the washers.

According to an aspect of this invention, the spacer beads are tapered beads and have a relatively wide base surface facing the associated one of the successive washers, and a relatively narrow flat nose surface facing against a like nose surface of the other of the pair of spacer beads. These beads each have an axially bore that is flared out towards the base surface, so that at the nose surface of the spacer bead, the axially bore has a small clearance over the steering cable, but a wide clearance at the base to prevent the spacer bead from binding on the steering cable.

In the preferred embodiments, the steering cable has a diameter of between about 0.015 and 0.030 inches, and the axial bore, at the nose surface of the spacer bead, has a clearance, or difference in diameter from the cable, of only about 0.005 to 0.007 inches.

The spacer beads can have a frustoconic outer wall, or can have a cylindrical wall towards the base and a spherical wall connecting the cylindrical wall to the nose surface.

Preferably, the flared portion of the spacer bead bore is a conic axial bore which opens toward the base surface with an apex angle of about forty degrees, and the nose surface has a diameter of about one-half to three-quarters the diameter of the base surface of the spacer bead.

The above and many other objects, features, and advantages of this invention will be more fully understood from the ensuing detailed description of a preferred embodiment, which should be considered in connection with the accompanying drawing.

DETAILED DESCRIPTION OF THE PREFERRED EMBODIMENTS

Figure 1:
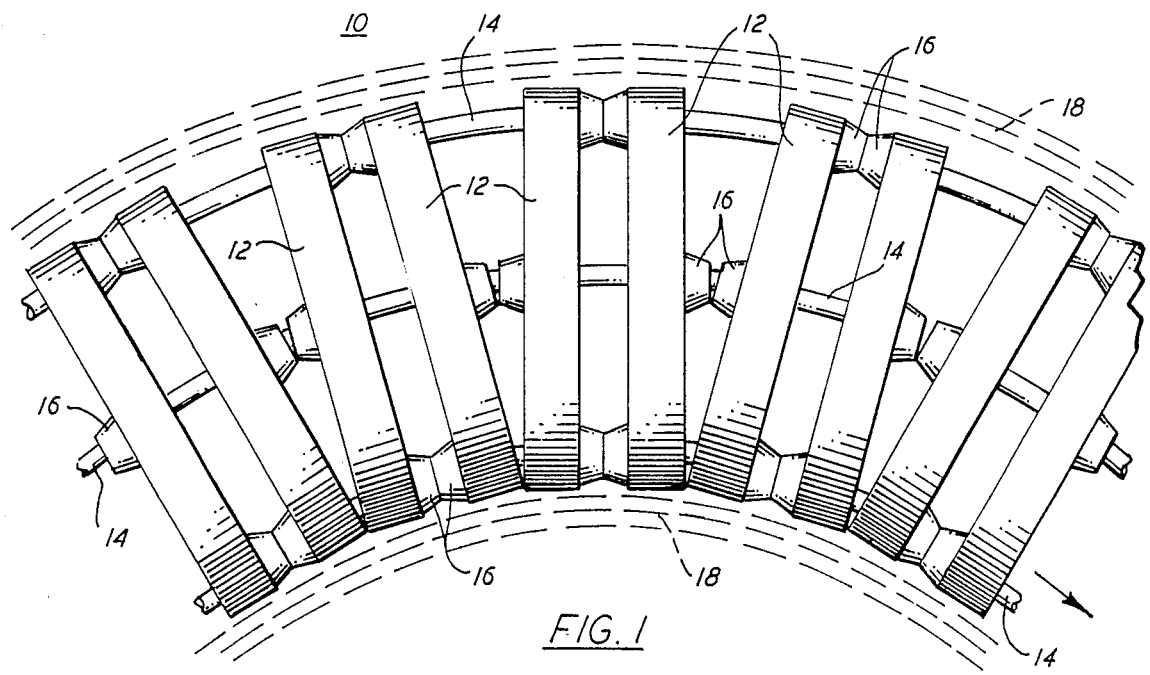
FIG. 1 is a sectional view of a steering section of an endoscope or borescope according to a first embodiment of this invention.
Figure 3:
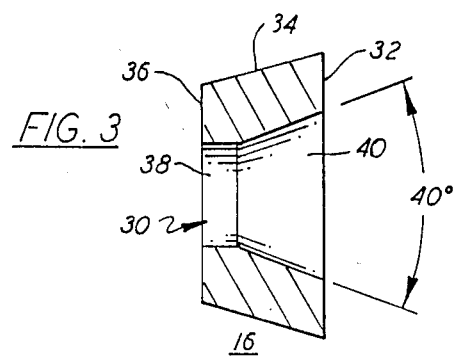
FIG. 3 is a sectional view of a spacer bead as employed in this first embodiment.
Figure 4:
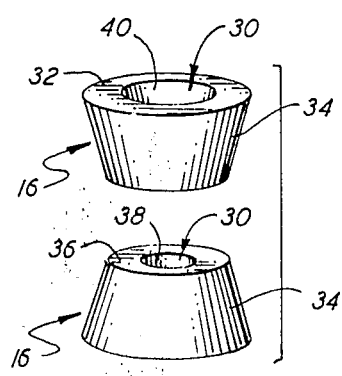
FIG. 4 is a perspective view of the spacer beads employed in the first embodiment.
Figure 5:
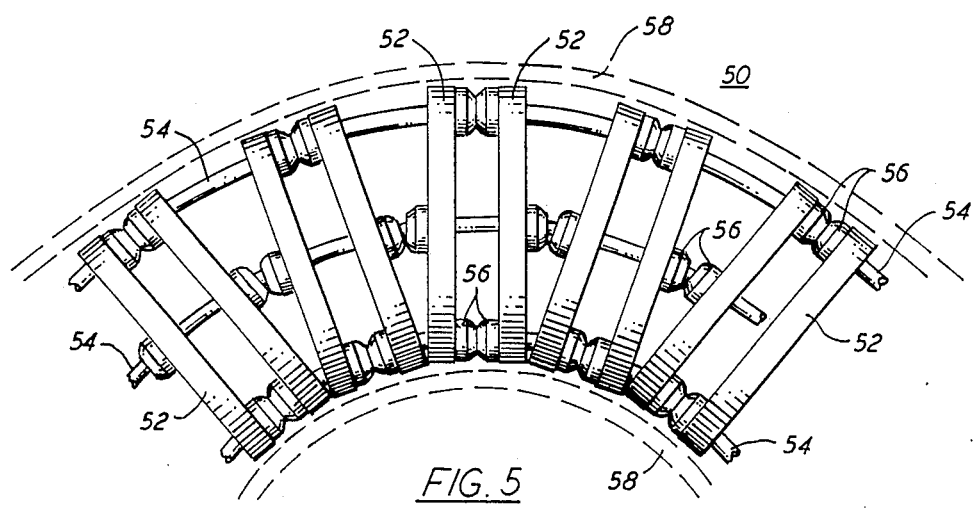
FIG. 5 is a sectional view of a steering section of an endoscope according to a second embodiment of this invention.

Referring now to the drawing, and initially to FIG. 1 thereof, a generally cylindrical steering section 10 of one type of endoscope has its proximal end (to the left in the drawing) connected to an elongated flexible tube, and on its distal end (to the right in the drawing) is mounted a video or fiber optics type viewing head (not shown). The steering section 10 is formed of a stack of washers 12, a typical one of which is shown in plan in FIG. 2. With these washers 12 there are associated two pairs of steering cables 14, which are preferably twisted strand stainless steel cables. The tapered-side spacer beads 16 (shown in section in FIG. 3 and in perspective in FIG. 4) are disposed over the cables 14 in the alternate spaces between the washers 12, i.e. at alternate pairs of the steering cables, considered in progression from one washer to the next. The assembly is covered with a flexible sheath 18.

Figure 2:
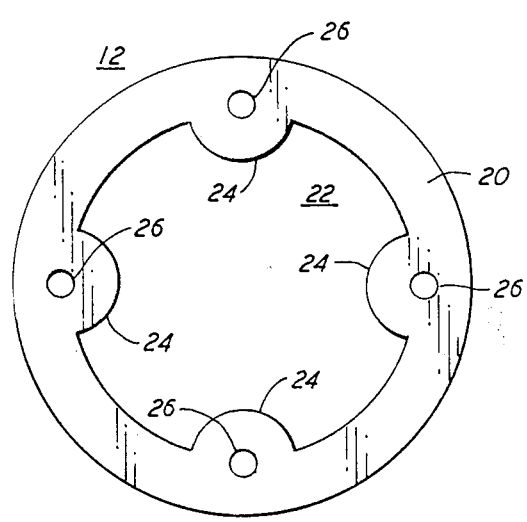
FIG. 2 is a plan view of a washer of the first embodiment.

The washers 12 as shown in FIG. 2 can favorably be composed of aluminum bronze or beryllium copper. The washers 12 are basically in the form of a circular ring 20 which has a generally cruciform central passage 22 defined among four inwardly directed lobes 24 that are spaced at 90 degree intervals on the ring 20. Peripheral through-bores 26 penetrate these lobes 24, and the steering cables 14 pass through these bores 26. The stack of washers 12 has respective bores aligned in registry with one another.

The spacer beads 16 each have an axial passage 30, a relatively wide base surface 32 that abuts a lobe 24 of the associated washers 12, a tapered sidewall 34, here a frustoconic surface, and a relatively narrow flat nose surface 36. The axial passage 30 has a cylindrical nose portion 38, which, as aforesaid, has a relatively small clearance over the associated steering cable 14, and a flared base portion 40 that expands baseward, here with an apex angle of forty degrees.

Pairs of these washers 16 are disposed in alternate inter-washer spaces on each of the steering cables 14, i.e., at the top and bottom in the drawing, and in the remaining spaces over the other two cables 14, that is, the front and back (obscured) in the drawing.

Each pair of these beads 16 has its nose surfaces 36 abutting one another. These beads 16 serve as pivots to define hinge lines for bending the steering section 10.

The cables 14 pass through the bores 26 and the bead through-passages 30, and slide relative to the beads 16 and the washers 12. The cables 14 are anchored to a point in the viewing head, and their displacement causes flexion of the steering section to bend the same in an arch, generally as indicated in FIG. 1, the general manner of which is well known.

The relatively small nose surfaces 36 of the facing spacer beads 16 rock with respect to one another to form generally smooth bending points, while the flat base surfaces 32 of the beads 16 seat against the lobes 24 of the washers 12. Because there is a very small clearance as between the nose portion 38 of the axial passage 30 and the associated cable 14, there is very small lateral play as between facing spacer beads 16. Consequently, the flat nose surfaces 36 of the beads 16 remain in engagement with one another despite their small size. Also, because the base portion 40 of the axial passage is countersunk or flared, the axial passage 30 will not bind against the associated cable 14, even during extreme bending of the section 10.

In this first embodiment, the endoscope is in the form of a gastroscope, having a nominal diameter of 9.5 millimeters. The diameter of the cables 14 is substantially 0.018 inches, and the diameter of the narrow nose portion 38 of the through-passage 30 is substantially 0.023 inches, to 0.025 inches. This provides a clearance of only about 0.005 to 0.007 inches.

The spacer beads 16 have a thickness dimension of about 0.021 inches, a width, at the nose portion, of 0.038 inches, and a width or diameter at the base portion of 0.050 inches. In this embodiment, the cylindrical nose portion 38 of the axial passage 30 has a length of about 0.006 inches.

By way of contrast, in corresponding spacers employed with respect to the endoscopes described in application Ser. No. 806,667, where the steering cables had a diameter of about 0.018 inches, the spacer bead had a through passage of 0.033 inches, which gave a clearance of about 0.015 inches.

A second embodiment of this invention is shown in FIGS. 5–8. In this second embodiment, elements that correspond to similar elements in the first embodiment are identified with corresponding reference numbers that are raised by 40.

Here, the endoscope is a large channel biopsy colonoscope, and its steering section 50 includes a stack of washers 52 (also shown in FIG. 6), two pairs of steering cables 54, associated pairs of spacer beads 56, and a flexible sheath 58.

As in the first embodiment, the washers 52 are formed of a ring 60 with a generally cruciform inner passageway 62 defined among four lobes 64 spaced at 90 degree intervals. A through-bore 66, through which an associated one of the steering cables 54 passes, is centered in each of the lobes 64.

Figure 7:
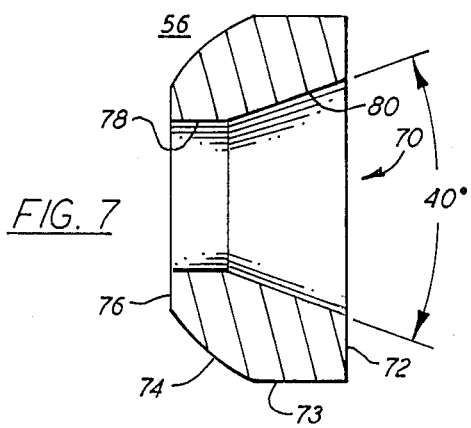
FIG. 7 is a sectional view of a spacer bead employed in the second embodiment.
Figure 6:
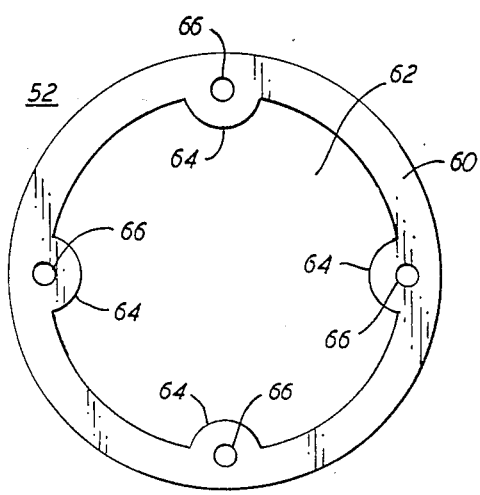
FIG. 6 is a plan view of a washer of the second embodiment.
Figure 8:
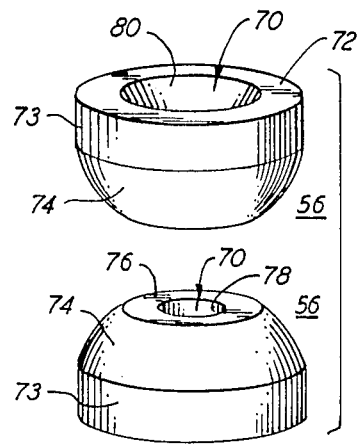
FIG. 8 is a perspective view of the spacer beads as employed in the second embodiment.

The spacer beads 56, shown in section in FIG. 7 and in perspective view in FIG. 8, each have a central axial passage 70, a relatively wide flat base surface 72, a cylindrical side surface 73, rising part way from the base surface 72 in the thickness direction of the bead 56, and a spherical surface 74 which extends from the cylindrical surface 73 to a relatively narrow, flat nose surface 76 of the bead 56. As in the first embodiment, the axial passageway 70 has a small-clearance cylindrical nose portion 78 and a flared or countersunk base portion 80 which opens outward towards the base of the bead 56. The beads 56 are disposed in pairs in nose-to-nose configuration, with the nose surfaces 76 bearing upon one another, and the base surfaces 72 disposed against the corresponding lobes 64 of the associated washers 52.

In this embodiment, the steering cables 54 have a cable diameter of about 0.027 inches, and the nose portion 78 of the axial passage 70 has a diameter of about 0.032 to about 0.034 inches. This provides a clearance of about 0.005 to 0.007 inches. By contrast, in previous spacer bead arrangements employing an 0.027 inch diameter steering cable, the spacer bead had a passage of 0.042 to 0.044 inches, which provided a clearance of 0.015 inches.

As further shown in this embodiment, the spacer beads 56 have a thickness dimension of about 0.038 inches, the base surface has the diameter of about 0.080 inches, and the nose surface 76 has a diameter of about 0.047 inches. The neck portion 78 of the axial passage 70 has a thickness of about 0.0125 inches, and the countersunk or flared portion has an apex angle of about forty degrees. Also, the spherical surface 74 has a radius of curvature of 0.0465 inches centered at the geometrical center of the base surface 72.

The beads 16 and 56 of these embodiments can be formed of a suitable metal, such as beryllium copper, aluminum bronze or any other metal exhibiting similar hardness or wear resistance.

While the above description relates to specific preferred embodiments of this invention, it is clear that many modifications and variations thereof would be apparent to those of skill in the art without departing from the scope and spirit of this invention, as defined in the appended claims.

We claim:

1. In a steerable endoscope or borescope of the type having a viewing head, a cable-bendable steering section proximally of the viewing head and including a flexible sheath, a plurality of axially aligned flat washers each having a central passage and a plurality of peripheral bores therethrough, pairs of which are generally diametrically disposed, a plurality of steering cables passing through respective axially aligned peripheral bores of said washers, and pairs of spacer beads disposed at the locations of at least certain peripheral bores associated with certain ones of said steering cables and serving to define bending locations for said steering section such that displacement of one opposed pair of the steering cables results in bending of the steering section; the improvement wherein said spacer beads are tapered beads disposed over said certain ones of said cables and have a relatively wide base surface facing the associated one of the successive washers and a relatively narrow flat nose surface facing a like nose surface of the other of the pair of spacer beads, wherein said beads each have an axial bore therein that is flared out towards said base surface to prevent said spacer bead from binding on said steering cable.

2. The steerable endoscope of claim 1 wherein said cable has a predetermined cable diameter of between about 0.015 and 0.030 inches, and said axial bore at the nose surface of the spacer bead has a diameter of only about 0.005 to 0.007 inches greater than the cable diameter.

3. The steerable endoscope of claim 1 wherein said cables have a diameter of about 0.027 inches, and the axial bores of the spacer beads at the nose surface thereof have a diameter of about 0.032 inches.

4. The steerable endoscope of claim 3 wherein said spacer beads have an axial thickness of substantially 0.038 inches, a diameter at the nose surface of substantially 0.047 inches, and a diameter at the base surface of substantially 0.080 inches.

5. The steerable endoscope of claim 1 wherein said cables have a diameter of about 0.018 inches, and the axial bores of said spacer beads at the nose surface thereof have a diameter of about 0.023 inches.

6. The steerable endoscope of claim 5 wherein said spacer beads have an axial thickness of substantially 0.021 inches, a diameter at the nose surface of substantially 0.038 inches, and a diameter at the base surface of substantially 0.050 inches.

7. The steerable endoscope of claim 1 wherein said pairs of spacer beads are disposed at alternate pairs of said steering cables, considered in progression from one said washer to the next.

8. In a steerable endoscope or borescope of the type having a viewing head, a cable-bendable steering section proximally of the viewing head and including a flexible sheath, a plurality of axially aligned flat washers each having a central passage and a plurality of peripheral bores therethrough, pairs of which are generally diametrically disposed, a plurality of steering cables passing through respective axially aligned peripheral bores of said washers, and pairs of spacer beads disposed at the locations of at least certain peripheral bores associated with certain ones of said steering cables and serving to define bending locations for said steering section such that displacement of one opposed pair of the steering cables results in bending of the steering section; the improvement wherein said spacer beads are tapered beads disposed over said certain ones of said cables and have a relatively wide base surface facing the associated one of the successive washers and a relatively narrow flat nose surface facing a like nose surface of the other of the pair of spacer beads, wherein said spacer beads have a frustoconic outer wall.

9. In a steerable endoscope or borescope of the type having a viewing head, a cable-bendable steering section proximally of the viewing head and including a flexible sheath, a plurality of axially aligned flat washers each having a central passage and a plurality of peripheral bores therethrough, pairs of which are generally diametrically disposed, a plurality of steering cables passing through respective axially aligned peripheral bores of said washers, and pairs of spacer beads disposed at the locations of at least certain peripheral bores associated with certain ones of said steering cables and serving to define bending locations for said steering section such that displacement of one opposed pair of the steering cables results in bending of the steering section; the improvement wherein said spacer beads are tapered beads disposed over said certain ones of said cables and have a relatively wide base surface facing the associated one of the successive washers and a relatively narrow flat nose surface facing a like nose surface of the other of the pair of spacer beads, wherein said spacer beads have a generally cylindrical outer wall rising from the base surface, and a spherical wall connecting the cylindrical wall to said nose surface.

10. In a steerable endoscope or borescope of the type having a viewing head, a cable-bendable steering section proximally of the viewing head and including a flexible sheath, a plurality of axially aligned flat washers each having a central passage and a plurality of peripheral bores therethrough, pairs of which are generally diametrically disposed, a plurality of steering cables passing through respective axially aligned peripheral bores of said washers, and pairs of spacer beads disposed at the locations of at least certain peripheral bores associated with certain ones of said steering cables and serving to define bending locations for said steering section such that displacement of one opposed pair of the steering cables results in bending of the steering section; the improvement wherein said spacer beads are tapered beads disposed over said certain ones of said cables and have a relatively wide base surface facing the associated one of the successive washers and a relatively narrow flat nose surface facing a like nose surface of the other of the pair of spacer beads, wherein said spacer beads have a conic axial bore therein which opens towards the base surface.

11. The steerable endoscope of claim 10 wherein said conic axial bore has an apex angle of about 40 degrees.

12. The steerable endoscope of claim 10 wherein said spacer beads also have a cylindrical axial bore connecting the nose surface with the conic axial bore.

13. In a steerable endoscope or borescope of the type having a viewing head, a cable-bendable steering section proximally of the viewing head and including a flexible sheath, a plurality of axially aligned flat washers each having a central passage and a plurality of peripheral bores therethrough, pairs of which are generally diametrically disposed, a plurality of steering cables passing through respective axially aligned peripheral bores of said washers, and pairs of spacer beads disposed at the locations of at least certain peripheral bores associated with certain ones of said steering cables and serving to define bending locations for said steering section such that displacement of one opposed pair of the steering cables results in bending of the steering section; the improvement wherein said spacer beads are tapered beads disposed over said certain ones of said cables and have a relatively wide base surface facing the associated one of the successive washers and a relatively narrow flat nose surface facing a like nose surface of the other of the pair of spacer beads, wherein said spacer beads have a diameter about ½ to ¾ the diameter of the base surface.

* * * * *

UNITED STATES PATENT AND TRADEMARK OFFICE
CERTIFICATE OF CORRECTION

PATENT NO. : 4,796,607

DATED : January 10, 1989

INVENTOR(S) : Jimmie B. Allred, III and Richard Bingham

It is certified that error appears in the above-identified patent and that said Letters Patent is hereby corrected as shown below:

Claim 13, line 38, please change "spacer beads have" to --nose surface has--.

Signed and Sealed this

Eighth Day of August, 1989

Attest:

DONALD J. QUIGG

Attesting Officer

Commissioner of Patents and Trademarks